United States Patent [19]

Shu et al.

[11] Patent Number: 5,110,742

[45] Date of Patent: May 5, 1992

[54] INDIRECT POTENTIOMETRIC METHOD AND DILUENT FOR ANALYSIS OF LITHIUM

[75] Inventors: Frank R. Shu, La Habra Heights, Calif.; Chen-Yie Chien, Ashland, Mass.; Julie S. Kim, Placentia, Calif.

[73] Assignee: Beckman Instruments, Inc., Fullerton, Calif.

[21] Appl. No.: 600,453

[22] Filed: Oct. 19, 1990

[51] Int. Cl.$^5$ ................ G01N 27/327; G01N 27/333
[52] U.S. Cl. ...................................... 436/18; 436/79; 436/150; 436/182; 204/153.15
[58] Field of Search ............... 436/74, 79, 18, 150, 436/179, 182; 204/17, 153.15, 416–419

[56] References Cited

FOREIGN PATENT DOCUMENTS 2520497 10/1975 Fed. Rep. of Germany .

OTHER PUBLICATIONS

Oesch, U. et al., "Ion-Selective Membrane Electrodes for Clinical Use", *Clin. Chem.* 32:1488–1459 (1989).
Attiyat, A. et al., "Comparative Evaluation of Neutral and Proton . . . ", *Anal. Chem.* 60:2561–2564 (1988).
Kitazawa, S. et al., "Lithium-Selective Polymeric Electrodes . . . ", *Analyst* 110:295–299 (1985).
Gadzekpo, V. P. Y. et al., "Lipophilic Lithium Ion Carrier . . . ", *Anal. Chem.* 57:493–495.
Gadzekpo, V. P. Y. et al., "Problems in the Application . . . ", *Analyst*, 111:567–570 (1986).
Metzger, E. et al., "Ion Selective Liquid Membrane . . . ", *Anal. Chem.* 58:132–135 (1986).
Okorodudu, Anthony O. et al., "Evaluation of Three First-Generation . . . ", *Clin. Chem.*, 36/1:104–110 (1990).
Kimura, Keiichi et al., "Lithium Ion Selective Electrodes . . . ", *Anal. Chem.*, 59:2331–2334.
Mascini, Marco, "Uses of Known Addition . . . ", *Ion-Selective Electrode Rev.*, vol. 2, pp. 17–71.
"Introducing SYNCHRON EL-LISE Analyzer . . . ", Beckman Bulletin 6646.
Shu, F. et al., "An Indirect Potentionetric Method . . . ", *Methodology in Clinical Application of Blood-Gases, pH, Electrolytes and Sensor Technology*, vol. 12, pp. 261–268, Ed. R. F. Moran IFCC/WGSE-AACC-/EBGD Symposium, Monterey Bay, Ca. (Jul. 20, 1990).

*Primary Examiner*—David L. Lacey
*Assistant Examiner*—Daniel Redding
*Attorney, Agent, or Firm*—William H. May; Arnold Grant; Richard P. Burgoon, Jr.

[57] ABSTRACT

An indirect potentiometric method and diluent for the analysis of lithium are disclosed. The diluent includes effective amounts of a pH buffer, at least one lithium salt, and a non-cationic surfactant containing at least one hydrophobic group, at least one hydrophillic group and being substantially free of polyoxyethylene groups. Most preferably, the pH buffer is tris-(hydroxymethyl-)aminomethane-phosphate, the lithium salt is lithium chloride, and the surfactant is 2,4,7,9-tetramethyl-5-decyn-4,7 diol. An indirect potentiometric determination of lithium in a clinical sample comprises the steps of mixing the sample with a diluent, contacting an aliquot of the diluted sample with a lithium specific ion selective electrode and at least one ion selective electrode specifically responsive to a monovalent interfering ion, and measuring both the response of the lithium specific ion selective electrode and the monovalent interfering ion specific ion selective electrode, the responses being an indication of the concentration of lithium in the sample.

37 Claims, No Drawings

INDIRECT POTENTIOMETRIC METHOD AND DILUENT FOR ANALYSIS OF LITHIUM

FIELD OF THE INVENTION

This invention relates to clinical sample analytical methods, more particularly to methods for detection of a substance of interest in a clinical sample, and principally to diluents and methods useful in the analysis of lithium utilizing indirect potentiometric ion selective electrodes.

BACKGROUND OF THE INVENTION

Lithium, usually in the form of lithium carbonate, is commonly used for the treatment of manic and manic depressive patients. Although traces of lithium ion are distributed widely throughout the body, the major effect of exogenous lithium is upon the central nervous system (CNS). Unlike other antipsychotic pharmaceutical agents, lithium is not thought to possess any general sedative properties, and, in therapeutic amounts, CNS effects are not observed except during chronic administration of lithium in manic or manic-depressive patients. The exact therapeutic mechanism of lithium is not currently known, primarily because the pathophysiology of manic disorders is unknown.

Lithium ions are readily absorbed when given orally, and a plasma lithium peak is reached approximately 2-4 hours after ingestion of lithium carbonate. Lithium plasma levels are usually monitored at least twice weekly in order to maintain this level within the range of from about 0.5 to about 1.0 mmol/L; for severe cases of mania, however, the lithium plasma level may be increased to about 1.5 mmol/L. Therapeutic doses of lithium can cause fatigue, muscular weakness, slurred speech, atoxia, tremor of the hands, nausea, vomiting, diarrhea and thirst. At plasma levels above about 2.2 mmol/L, more serious toxic effects occur, with the CNS primarily affected, i.e., consciousness is impaired, coma may occur, muscular rigidity, hyperactive deep reflexes and marked tremor and muscular fasciculations are observed, epileptic seizures can occur, and EEG abnormalities are common. A lithium plasma level of about 5.0 mmol/L can be fatal. Accordingly, it is not only important, but essential, to know what such plasma level is in order to avoid the deleterious effects associated therewith.

Analysis of lithium in biological fluids (e.g. sera, plasma, urine, cerebro-spinal fluid, or whole blood) is hampered by the presence of other ionic compounds in such fluids, and in particular, sodium ions. This interference is most noticeable at lower lithium concentrations (for example, about 0.10 mmol/L). With respect to serum, the molar ratio of lithium to sodium is about 1:1500. Accordingly, one of the challenges facing those developing an assay method for serum lithium is to overcome the interference from such ions.

Flame photometry is one method for lithium analysis in clinical specimens. In flame photometry, atoms are excited to an energy level above their ground state by a flame. Upon return to ground state, the energy is released as radiation at a frequency characteristic of the element under investigation. By measuring the emission light intensity, the concentration of the analyte of interest in the sample can be determined. Despite its relative simplicity, flame photometry is a tedious procedure and includes several critical disadvantages as an analytical method, e.g., spectral interference between two or more substances in a sample (such as is the case with serum sodium and lithium), background interferences, anionic and cationic interferences, and self-absorption. Furthermore, routine maintenance of the instrumentation is not only critical to ensure good analytical results, but is itself a tedious procedure. Additionally, flame photometry instruments utilize air compressors, which on the whole are noisy, a distinct disadvantage in a clinical setting. Finally, there is the practical concern of safely storing a flammable gas in a laboratory environment.

Ion selective electrode (ISE) technology is an alternative to flame photometry which avoids many of these problems. ISE technology involves the use of a reference electrode and an ion selective electrode separated by a membrane. The ion selective electrode is specific or sensitive to the particular ion of interest. Typically, the reference electrode and the ion selective electrode are simultaneously immersed into a sample solution. An electrical potential is developed between the electrodes which is relative to the presence of the ion to which the ISE is sensitive or specific. This potential can be utilized to determine the concentration of that ion in the sample. Most often the investigator desires to only measure the concentration of one ion out of the many different ions in solution. Thus, the ion selective composition of the ISE, referred to as a "carrier" or "ionophore", must be capable of sequentially complexing the desired ion, transporting the complexed ion across the membrane, and releasing the ion, in preference to all other ions which may be present in the sample solution.

Macrocyclic polyethers, also referred to as cryptanols or "crown ethers", are well known lithium ion-complexing compounds which are suitable for use as ion selective electrodes. Such ionophores are described in, for example, U.S. Pat. No. 4,214,968; U.S. Pat. No. 4,504,368; Oesch, U. et al., "Ion Selective Membrane Electrodes for Clinical Use", *Clin. Chem.* 32:1448-1459 (1986); Kitayama, S. et al. "Lithium-Selective Polymeric Electrodes Based on Dodecylmethyl-14-Crown-4", *Analyst* 110:295-299 (1985); and, Attiyat, A. et al., "Comparative Evaluation of Neutral and Proton-Ionizable Crown Ether Compounds as Lithium in Ion-Selective Electrodes and in Solvent Extraction", *Anal. Chem.* 60:2561-2564 (1988). Other lithium ion complexing compounds are also available, and examples of these are described in U.S. Pat. No. 4,853,090; Gadzekpo, V. P. Y. et al., "Lipophilic Lithium Ion Carrier in a Lithium Ion Selective Electrode", *Anal. Chem.* 57:493-495 (1985); and, Gadzekpo, V.P.Y. et al., "Problems in the Application of Ion-Selective Electrodes to Serum Lithium Analysis", *Analyst,* 111:567-570 (1986). All of the preceding references of this paragraph are incorporated herein by reference.

Two methods are associated with ISE: the direct potentiometric method, where the sample is measured directly; and the indirect potentiometric method, where the sample is diluted prior to analysis. Of the two, the indirect potentiometric method is preferred because: (a) dilution of the sample derives the advantages of mass action law, (b) serum results do not usually correlate well between flame photometry and the direct potentiometric method, and (c) maintenance of a direct ISE analyzer is more difficult than an indirect ISE due to protein build-up on the direct ISE. However, despite the advantages of the indirect potentiometric methodology, there are no indirect potentiometric analyzers for lithium commercially available. This is based, in part, on the relationship of lithium in a clinical specimen to other ions therein. For example, in serum, where as previously noted the ratio of lithium to sodium is 1:1500, dilution of a serum sample makes analysis of the already miniscule amount of lithium present very difficult.

Thus, a need exists for an indirect ISE method for the determination of lithium in clinical samples. Additionally, because of the need to dilute the clinical sample for the indirect potentiometric analysis thereof, the diluent utilized is also important for proper analysis of lithium in clinical samples. Accordingly, a need also exists for a diluent useful in the indirect potentiometric determination of lithium in clinical samples.

SUMMARY OF THE INVENTION

The present invention advantageously satisfies both of the above listed needs.

A diluent in accordance with the present invention comprises effective amounts of a pH buffer, at least one lithium salt, and a non-cationic surfactant containing at least one hydrophobic group, at least one hydrophillic group, and being substantially free of polyoxyethylene groups. The pH of the diluent is within the range of about 5.5 to about 9.5.

An indirect potentiometric determination of lithium in a clinical sample in accordance with the present invention comprises the steps of mixing the sample with a diluent, contacting an aliquot of the diluted sample with a lithium specific ion selective electrode and an ion selective electrode specifically responsive to a monovalent interfering ion (for example, sodium or potassium), and measuring both the response of the lithium ion specific electrode and the monovalent interfering ion specific electrode, these responses being an indication of the concentration of the lithium in the sample. As used herein, the term "monovalent interfering ion" is an ion which interferes with ISE analysis of lithium.

DETAILED DESCRIPTION OF PREFERRED EMBODIMENTS

Methods for manufacturing ISEs are well known to those skilled in the art and will not be set forth in detail here. Reference is made to U.S. Pat. Nos. 4,770,759 and 4,853,090 which are incorporated herein by reference. A preferred lithium ionophore is 6,6 dibenzyl-14-crown-4 ether.

A diluent in accordance with the present invention comprises effective amounts of a pH buffer, at least one lithium salt, and a non-cationic surfactant containing at least one hydrophobic group, at least one hydrophillic group and being substantially free of polyoxyethylene groups. Preferably, the pH of the diluent is between about 5.5 and about 9.5. More preferably, the pH of the diluent is between about 6.0 and about 7.5. Most preferably, the pH of the diluent is about 7.0. The concentration of the pH buffer is at least about 0.1 mole per liter, and preferably between about 0.1 mole per liter and about 0.4 moles per liter. The percent by weight of the non-cationic surfactant is at least about 0.005. More preferably, the percent by weight of the non-cationic surfactant is between about 0.01 and about 0.05. The concentration of the lithium salt is preferably between about 0.025 millimole per liter and about 0.05 millimole per liter. Most preferably, 0.05 millimole per liter of lithium chloride is utilized.

Diluents heretofore used in indirect ISE analysis typically include therein surfactants or "wetting agents", which aid in the flow of the carrier solvent. Without surfactant, the solvent will not properly flow. Surfactants minimize bubble formation in the fluid delivery lines of instruments used for indirect ISE analysis. The surfactant must be compatible with the ionophore, i.e., a surfactant must not artificially alter the value of the selectivity coefficient. The term "selectivity coefficient" is a numerical value designating the preference of an ion selective electrode to a specific ion. Those skilled in the art typically will select a specified ion selective electrode having a relatively small selectivity coefficient, as this value indicates that the specific electrode has a stronger preference for the specified ion to the exclusion of other ions.

The surfactants heretofore used in the indirect ISE analysis of clinical samples have included polyoxyethylene (23) lauryl ether, available under the brand name Brij 35 TM, and polyoxyethylene octylphenyl ether, available under the brand name Triton X-100 TM. However, it has been determined that these surfactants have an adverse effect on the selectivity of lithium specific ion selective electrodes. While not wishing to be bound by any theory, it is believed that the polyoxyethylene groups of these surfactants may promote formation of crown ether-sodium complexes. Such complexes would be transported across the ISE membrane along with crown ether-lithium complexes and thus give a false reading for the lithium ion concentration.

It has been advantageously discovered that diluents including therein effective amounts of noncationic surfactants which do not contain polyoxyethylene groups and which include at least one hydrophobic group and at least one hydrophillic group do not interfere with the indirect potentiometric analysis of lithium. Preferably, the hydrophobic group is selected from the group consisting of alkyl groups having up to 12 carbon atoms and a moiety of at least two alkyl groups and at least one acetylinic bond. More preferably, the hydrophobic group is a moiety of at least two alkyl groups having at least one acetylinic bond. Preferably, the hydrophillic group is selected from the group consisting of hydroxyls, glycols, carboxylic acids, and sulfonic acids. More preferably the hydrophillic group is an hydroxyl group. A more preferred surfactant is selected from the group consisting of dimethyl octynediol, 2, 4, 7, 9-tetramethyl-5-decyn-4,7-diol, and lauric acid ($C_{12}H_{24}COOH$). Most preferably, the surfactant is 2,4,7,9-tetramethyl-5-decyn-4,7-diol. The aforementioned dimethyl octynediol and 2,4,7,9-tetramethyl-5-decyn-4,7-diol surfactants are commercially available under the brand names Surfynol 82 TM and Surfynol 104 TM, respectively (Air Products, Allentown, Pennsylvania).

The pH buffer comprises at least one of the following either singularly or in combination: acetic acid, 2-(N-morpholino)ethanesulfonic acid, 3-(N-morpholino) propanesulfonic acid, N-2-hydroxyethyl piperazene-N'-2-ethanesulfonic acid, phosphoric acid, N-[tris-(hydroxymethyl)methyl]glycine, tris(hydroxymethyl)aminomethane, triethyl amine, diethyl amine, dimethyl amine, and the alkyl amines having up to 12 carbon atoms. Most preferably, the pH buffer is tris-(hydroxymethyl) aminomethane-phosphate.

The volume to volume dilution ratio of the clinical sample to the diluent is preferably between about 1:10 to about 1:40. Most preferably, the dilution ratio is about 1:20. Dilution of a clinical sample already having low concentrations of lithium therein, e.g. serum, can effectively place the diluted sample-lithium concentration into the non-linear range of the lithium ion selective electrode. As such, the diluent most preferably incorporates therein at least one lithium salt, in an amount effective to correct for a decrease in sensitivity of the lithium specific non-selective electrode associated with the dilution of the sample. The concentration of the lithium salt is preferably between about 0.025 millimole per liter and about 0.075 millimole per liter. Most preferably, 0.05 millimole per liter of lithium-chloride is used. The lithium salt added to the diluent is referred to as a "spiking factor" or "S.F.".

Other optional addenda may be added to the diluent that do not interfere with the overall utility of the diluent. For example, it is desirable to include an effective amount of preservative within the diluent. A preferred preservative is 2-phenoxy ethanol. The percent by weight of the preservative is preferably between about 0.1 to about 0.4. Most preferably, the percent by weight of the preservative is about 0.2.

An indirect potentiometric determination of lithium in a clinical sample in accordance with the present invention comprises the steps of mixing the sample with the disclosed diluent, contacting an aliquot of the diluted sample with a lithium specific ion selective electrode and at least one ion selective electrode specifically responsive to a monovalent interfering ion (for example, sodium or potassium), and measuring both the response of the lithium specific ion selective electrode and the monovalent interfering ion specific ion specific electrode, these responses being an indication of the concentration of the lithium in the sample. Measuring the responses of both the lithium ion specific electrode and the monovalent interfering ion specific electrode need not be simultaneously accomplished and the order of response measurement is not critical to the method. Most preferably, the monovalent interfering ion is sodium because sodium ions cause the greatest interference with lithium ion selective electrodes. A modified Nicolskii-Eisenman equation (which is used to determine the concentration of an ion in solution based upon EMF values derived from that ion in solution) can be used to determine the concentration of lithium in the sample. Details as to the use of the modified Nicolskii-Eisenman equation, and the manner in which the concentration of lithium in a test sample can be determined, are set forth in Example II.

EXAMPLES

The following examples directed to preferred embodiments of the invention disclosed herein are not intended, nor should they be construed, as limiting the disclosure, or the claims to follow.

I. Reagent Analysis

A. Surfactant Effect On The Ion Selective Electrode

Analysis of surfactant effect was conducted on a System E2A TM indirect potentiometric analyzer (Beckman Instruments, Inc., Brea, CA.), which is useful in the determination of sodium and potassium concentration in solution. For these examples, the potassium ISE was replaced with a lithium ISE.

Diluents tested included the following ingredients:

| Ingredient | Concentration |
|---|---|
| A) Tris* | 0.3 mole/L |
| B) Phosphoric acid | 0.15 mole/L |
| C) Lithium-chloride | 0.05 mmol/L |
| D) Surfactant | (varies) |

-continued

| Ingredient | Concentration |
|---|---|
| E) 2-phenoxy ethanol | 0.2% |
| pH = 7.0 | |

*tris-(hydroxymethyl)aminomethane

With respect to the surfactant, four conditions were separately analyzed: (1) no surfactant; (2) 2,4,7,9-tetramethyl-5-decyn-4,7-diol (0.02%); (3) Brij 35 TM (0.01%); and (4) Triton X-100 TM (0.005%). The percent by weight amounts of the Brij 35 and Triton X-100 TM surfactants were in accordance with the manufacturers' recommended amounts. Calibration solutions including lithium therein were diluted one part to 20 parts diluent.

After analysis on the aforementioned E2A analyzer, selectivity coefficients for the lithium specified ion selective electrode were derived for each surfactant tested. Values thereof are set forth in Table I:

TABLE I

| Selectivity Coefficient Values | | |
|---|---|---|
| | Surfactant | $K_{Li,Na}^{Pot}$ |
| (1) | None | 0.0041 |
| (2) | 2,4,7,9-tetramethyl-5-decyn-4,7-diol | 0.0040 |
| (3) | Brij 35 TM | 0.1021 |
| (4) | Triton X-100 TM | 0.2555 |

The selectivity coefficient of the lithium specific ion selective electrode was not affected by the inclusion of the most preferred surfactant in the diluent. However, the selectivity coefficient value was increased by a factor of 25 when Brij 35 TM was utilized, and by a factor of 62 when Triton X-100 TM was utilized.

B. Surfactant Effect - Polyoxyethylene Group

Separate comparative testing between surfactants differing in the inclusion of polyoxyethylene groups were also conducted. The parameters and diluents set forth in Example I.A. were utilized. The surfactants tested were (a) 2,4,7,9-tetramethyl-5-decyn-4,7 diol (0.02%); and (b) ethoxylated tetramethyldecyndiol (0.02%), which is the reaction product of ethylene oxide with 2,4,7,9-tetramethyl-5-decyn-4,7-diol. The surfactants can be represented as follows:

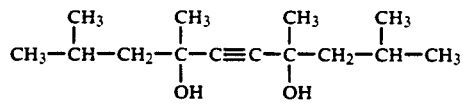

(b) ethoxylated tetramethyldecyndiol

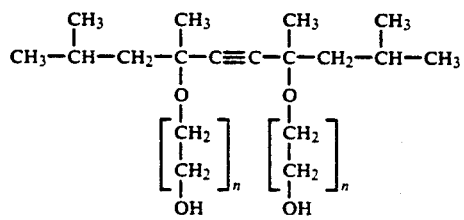

the primary difference between the surfactants is the inclusion of polyoxyethylene groups in surfactant (b).

After analysis on the aforementioned E2A TM analyzer, selectivity coefficients for the lithium specific ion selective electrode were derived. Values thereof are set forth in Table II:

TABLE II

| Selectivity Coefficient Values | |
|---|---|
| Surfactant | $K_{Li,Na}^{pot}$ |
| 2,4,7,9,-tetramethyl-5-decyn 4,7-diol | .0117 |
| ethoxylated tetramethyldecyndiol | .0292 |

As the above data indicates, a surfactant including polyoxyethylene groups adversely interferes with the selectivity coefficient of the lithium specific ion selective electrode.

C. Spiking Factor Effect

Serum pools (Beckman Instruments, Inc., Brea, CA.) from healthy individuals were spiked with different amounts of lithium carbonate. Analysis of the spiked pools for lithium ion concentration was performed using an Instrumentation Laboratory Model 943 Flame Photometer. Thereafter, the same spiked pools were analyzed on the aforementioned E2A ™ analyzer; prior to analysis, pools were diluted in a 1:20 volume-to-volume ratio of pool to diluent (as defined above, with 0.02% of the most preferred surfactant). Serum correlations were made between litium recovery as determined by flame photometry, and serum diluted with diluent including 0.05 mmol/L lithium chloride as a spiking factor ("S.F.") and diluent not including the spiking factor. Lithium recovery values (in mmol/L) are set forth in Table II:

TABLE II

| Spiking Factor Effect | | |
|---|---|---|
| | Lithium Recovery Indirect ISE | |
| Sample | Lithium Recovery Flame Photometry | With S.F. | Without S.F. |
| 1 | 0.10 | .14 | 0.23 |
| 2 | 0.50 | .50 | 0.47 |
| 3 | 1.00 | .98 | 0.86 |
| 4 | 2.55 | 2.57 | 2.59 |
| 5 | 5.05 | 5.13 | 5.77 |

$Y_{ISE-S.F.} = 0.9751 \times X_{FP} + 0.0571$
$R^2 = .9930$
n = 108

Recovery values using an indirect potentiometric method were more closely aligned with those derived by the flame photometric method when the spiking factor was utilized, particularly at the lower concentration level of 0.10 mmol/L. The serum correlation between the indirect potentiometric methodology utilizing the preferred diluent including the spiking factor (indicated as "ISE-S.F."), and flame photometry (indicated as "FP") supports this position.

The above data of Examples I.A, I.B, and I.C demonstrates that the disclosed diluent allows for analysis of lithium by an indirect potentiometric method. This data further demonstrates that the use of at least one lithium salt as a spiking factor in the diluent improves the recovery of lithium in the indirect potentiometric measuring system.

II. Determination of Lithium Concentration In Serum Sample

Because the diluent incorporates therein a lithium spiking factor ("S.F."), when such an S.F. is utilized, the Nicolskii-Eisenman equation is modified as follows:

$$E_{Li} = E_o + S \log [C_{Li} - K_{Li,Na} \times C_{Na}) - SF] \quad (1)$$

where $E_{Li}$ is the value (in mV) of the lithium ISE towards lithium ions in solution; $E_o$ is a constant EMF difference (temperature dependent); S is the slope of the electrical response function; $K_{Li,Na}$ is the selectivity coefficient of the lithium-specific ISE; S.F. is the value of the spiking factor; and CLi and CNa are the concentrations of lithium and sodium in the sample (the major source of interference to a lithium ISE is from sodium ion). The S.F. value is a combination of both the amount of the lithium salt added to the diluent and a system "carry-over" value attributed to residual lithium which may remain on the lithium ISE or flow cell. The concentration of lithium in the test sample can be determined using the following equation:

$$C_{Li} = antilog[(E_{Li} - E_o)/S] - [(K_{Li,Na} \times C_{Na}) - SF] \quad (2)$$

For a preferred analysis of serum lithium concentration, an automatic electrolyte system capable of determining the concentrations of several different electrolytes is utilized; such a system is preferred in that analysis of different monovalent ions in a sample allows for computation of the concentration of an ion that interferes in the analysis of the desired ion, this concentration being useful for the determination of the selectivity coefficient. A preferred analyzer is a SYNCHRON® EL-ISE ™ analyzer (available from Beckman Instruments, Inc., Fullerton, CA), which analyzer follows an indirect potentiometric methodology, although the invention is not to be limited in its applicability to this preferred analyzer.

Most preferably, a 50ul sample of, e.g. plasma or serum, is diluted 20 fold with the diluent disclosed herein. For analysis of the diluted sample, the aforementioned analyzer measures the lithium electrode response of the sample (by means of the preferred lithium specific ISE); this value is represented as $E_{Li}$. The preferred analyzer can also determine a sodium electrode response of the sample ($E_{Na}$). Because sodium ISEs are highly selective, $C_{Na}$ is readily determined by standard techniques. By determining values for $E_{Li}$, $E_{Na}$, and $C_{Na}$, the concentration of lithium in the sample can be determined using Equation (2).

The foregoing examples demonstrate the advantageous, usefulness and feasibility of determining the concentration of lithium in a clinical sample using an indirect potentiometric methodology, based upon the novel diluent and methodology disclosed herein.

While the foregoing examples have described the invention in terms of preferred embodiments and have referenced a preferred instrument for analysis, it should be understood that the invention disclosed herein not to be limited to the specific forms or applications shown. Accordingly, equivalents and modifications which are within the purview of the skilled artisan are considered to be a part of this disclosure and the claims that follow.

What is claimed is:

1. A diluent useful for the indirect potentiometric determination of lithium in a clinical sample comprising, in effective amounts:
   (i) a pH buffer;
   (ii) at least one lithium salt; and
   (iii) a non-cationic surfactant, said surfactant containing at least one hydrophobic group and at least one hydrophillic group, and being substantially free of polyoxyethylene groups;

the pH of said diluent being within the range of about 5.5 to about 9.5.

2. The diluent of claim 1 wherein said hydrophobic group is selected from the group consisting of alkyl groups having up to 12 carbon atoms, and a moiety of at least two alkyl groups and at least one acetylinic bond.

3. The diluent of claim 1 wherein said hydrophobic group is a moiety of at least two alkyl groups having at least one acetylinic bond.

4. The diluent of claim 1 wherein said hydrophillic group is selected from the group consisting of hydroxyls, glycols, carboxylic acids, and sulfonic acids.

5. The diluent of claim 1 wherein the hydrophillic group is an hydroxyl.

6. The diluent of claim 1 wherein the non-cationic surfactant is selected from the group consisting of dimethyl octynediol, 2, 4, 7, 9-tetramethyl-5-decyn-4,7-diol, and lauric acid.

7. The diluent of claim 1 wherein the non-cationic surfactant is 2, 4, 7, 9-tetramethyl-5-decyn-4,7-diol.

8. The diluent of claim 1 wherein the pH buffer is selected from the group consisting of acetic acid, 2-(N-morpholino)ethanesulfonic acid, 3-(N-morpholino) propanesulfonic acid, N-2-hydroxyethyl piperazene-N'-2-ethanesulfonic acid, phosphoric acid, N-[tris-(hydroxymethyl)methyl]glycine, tris-(hydroxymethyl)aminomethane, triethyl amine, diethyl amine, dimethyl amine, and the alkyl amines having up to 12 carbon atoms.

9. The diluent of claim 1 wherein the pH buffer is tris-(hydroxymethyl)aminomethane-phosphate.

10. The diluent of claim 1 wherein the concentration of said pH buffer in said diluent is at least about 0.1 mole per liter.

11. The diluent of claim 1 wherein the concentration of said pH buffer in said diluent is between about 0.1 mole per liter and about 0.4 moles per liter.

12. The diluent of claim 1 wherein the percent by weight of said non-cationic surfactant in said diluent is at least about 0.005.

13. The diluent of claim 1 wherein the percent by weight of said non-cationic surfactant in said diluent is between about 0.01 and about 0.05.

14. The diluent of claim 1 wherein the concentration of said lithium salt in said diluent is between about 0.025 millimole per liter and about 0.075 millimole per liter.

15. The diluent of claim 1 wherein said lithium salt is lithium chloride.

16. The diluent of claim 15 wherein the concentration of lithium chloride in said diluent is about 0.05 millimol per liter.

17. An indirect potentiometric method for the determination of the concentration of lithium in a clinical sample comprising the steps of:
(a) mixing said sample with a diluent, said diluent comprising:
(i) a pH buffer,
(ii) at least one lithium salt, and
(iii) a non-cationic surfactant, said surfactant containing at least one hydrophobic group, at least one hydrophillic group, and being substantially free of polyoxyethylene groups;
the pH of said diluent being within the range of about 5.5 to about 9.5, said mixing forming a diluted sample;
(b) contacting an aliquot of said diluted sample with a lithium specific ion selective electrode and at least one ion selective electrode specifically responsive to a monovalent interfering ion;
(c) measuring the response of said lithium ion specific electrode and measuring the response of said monovalent interfering ion specific electrode, the concentration of said lithium in said sample is calculated based on the response of said electrodes.

18. The method of claim 17 wherein said monovalent interfering ion is sodium.

19. The method of claim 17 wherein the volume to volume ratio of said sample to said diluent is between about 1:10 and about 1:40.

20. The method of claim 17 wherein the volume to volume ratio of said sample to said diluent is about 1:20.

21. The method of claim 17 wherein the concentration of said pH buffer in said diluent is at least about 0.1 mole per liter.

22. The method of claim 17 wherein the concentration of said pH buffer in said diluent is between about 0.1 mole per liter to about 0.4 moles per liter.

23. The method of claim 17 wherein the percent by weight of said non-cationic surfactant in said diluent is at least about 0.005.

24. The method of claim 17 wherein the percent by weight of said non-cationic surfactant in said diluent is between about 0.01 and about 0.05.

25. The method of claim 17 wherein the concentration of said lithium salt in said diluent is between about 0.025 millimole per liter and about 0.075 millimole per liter.

26. The method of claim 17 wherein said lithium salt is lithium chloride.

27. The method of claim 26 wherein the concentration of said lithium chloride in said diluent is about 0.05 millimole per liter.

28. A diluent useful in the indirect potentiometric determination of lithium in a clinical sample comprising, in effective amounts,:
(i) a pH buffer,
(ii) at least one lithium salt, and
(iii) a non-cationic surfactant selected from the group consisting of dimethyl octynediol, 2, 4, 7, 9-tetramethyl -5-decyn -4,7,-diol, and lauric acid;
the pH of said diluent being within the range of about pH 5.5 to about pH 9.5.

29. The diluent of claim 28 wherein the pH buffer is selected from the group consisting of acetic acid, 2-(N-morpholino)ethanesulfonic acid, 3-(N-morpholine) propanesulfonic acid, N-2-hydroxyethyl piperazene-N'-2-ethanesulfonic acid, phosphoric acid, N-[tris-(hydroxymethyl)methyl] glycine, tris-(hydroxymethyl)aminomethane, triethyl amine, diethyl amine, dimethyl amine, and the alky amines having up to 12 carbon atoms.

30. The diluent of claim 28 where the pH buffer is tris(hydroxymethyl)aminomethane-phosphate.

31. The diluent of claim 28 wherein the concentration of said pH buffer in said diluent is at least about 0.1 mole per liter.

32. The diluent of claim 28 wherein the concentration of said pH buffer in said diluent is between about 0.1 mole per liter to about 0.4 moles per liter.

33. The diluent of claim 28 wherein the percent by weight of said non-cationic surfactant in said diluent is at least about 0.005.

34. The diluent of claim 28 wherein the percent by weight of said non-cationic surfactant in said diluent is between about 0.01 and about 0.05.

35. The diluent of claim 28 wherein the concentration of said lithium salt in said diluent is between about 0.025 millimole per liter to about 0.075 millimole per liter.

36. The diluent of claim 28 wherein said lithium salt is lithium chloride.

37. The diluent of claim 36 wherein the concentration of said lithium chloride in said diluent is about 0.05 millimole per liter.

* * * * *